United States Patent [19]

Buscemi et al.

[11] Patent Number: 5,464,450
[45] Date of Patent: Nov. 7, 1995

[54] BIODEGRADABLE DRUG DELIVERY VASCULAR STENT

[75] Inventors: Paul J. Buscemi, Long Lake; Elizabeth A. Stejskal, St. Paul; Donald F. Palme, II, Dayton; Lixiao Wang, St. Paul, all of Minn.

[73] Assignee: SCIMED Lifesystems Inc., Maple Grove, Minn.

[21] Appl. No.: 215,206

[22] Filed: Mar. 21, 1994

Related U.S. Application Data

[63] Continuation of Ser. No. 13,145, Feb. 1, 1993, abandoned, which is a continuation of Ser. No. 771,655, Oct. 4, 1991, abandoned.

[51] Int. Cl.$^6$ .............................. A61F 2/06; A61F 2/04; A61M 29/02
[52] U.S. Cl. .............................. 623/6; 623/12; 606/154; 606/195
[58] Field of Search ...................... 623/1, 11, 12; 606/191–200, 151–158; 600/36; 604/890.1, 891.1, 8, 104

[56] References Cited

U.S. PATENT DOCUMENTS

| | | | |
|---|---|---|---|
| 3,636,956 | 1/1972 | Schneider | 128/335 |
| 3,799,172 | 3/1974 | Szpur | 128/349 |
| 3,975,371 | 8/1976 | Lednicer et al. | 260/198 |
| 4,141,364 | 2/1979 | Schultze | 128/349 |
| 4,183,102 | 1/1980 | Guiset | 3/1.4 |
| 4,580,447 | 11/1985 | Seiler, Jr. et al. | 623/1 |
| 4,580,568 | 4/1986 | Gianturco | 128/348 |
| 4,681,110 | 7/1987 | Wiktor | 128/343 |
| 4,690,684 | 9/1987 | McGreevy et al. | 623/12 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,753,236 | 6/1988 | Healey | 128/334 |
| 4,768,507 | 9/1988 | Fischell et al. | 128/303 |
| 4,770,176 | 9/1988 | McGreevy et al. | 128/334 |
| 4,776,337 | 10/1988 | Palmaz | 128/343 |
| 4,787,399 | 11/1988 | Bonello et al. | 128/772 |
| 4,787,899 | 11/1988 | Lazarus | 623/1 |
| 4,792,336 | 12/1988 | Hlavacek et al. | 623/13 |
| 4,795,458 | 1/1989 | Regan | 623/1 |
| 4,820,298 | 4/1989 | Leveen et al. | 623/1 |
| 4,830,003 | 5/1989 | Wolff et al. | 128/343 |
| 4,850,999 | 7/1989 | Planck | 623/1 |
| 4,871,365 | 10/1989 | Dumican | 623/13 |
| 4,877,030 | 10/1989 | Beck et al. | 623/1 |
| 4,886,062 | 12/1989 | Wiktor | 128/343 |
| 4,892,098 | 1/1990 | Sauer | 606/18 |
| 4,907,336 | 3/1990 | Gianturco | 29/515 |
| 4,923,470 | 5/1990 | Dumican | 623/13 |
| 4,942,875 | 7/1990 | Hlavacek et al. | 623/13 |
| 4,957,508 | 9/1990 | Kaneko et al. | 623/12 |
| 4,990,155 | 2/1991 | Wilkoff | 606/191 |
| 4,990,158 | 2/1991 | Kaplan et al. | 623/1 |
| 4,994,033 | 2/1991 | Shockey et al. | 604/101 |
| 4,997,440 | 3/1991 | Dumican | 623/13 |
| 5,019,096 | 5/1991 | Fox, Jr. et al. | 623/1 |
| 5,059,211 | 10/1991 | Stack et al. | 623/1 |
| 5,078,736 | 1/1992 | Behl | 623/1 |
| 5,147,400 | 9/1992 | Kaplan et al. | 623/13 |

FOREIGN PATENT DOCUMENTS

| | | |
|---|---|---|
| 2005199 | 12/1989 | Canada . |
| 2008312 | 1/1990 | Canada . |
| 2025626 | 9/1990 | Canada . |
| 0246998 | 11/1987 | European Pat. Off. . |
| 0246998A2 | 11/1987 | European Pat. Off. . |

*Primary Examiner*—Debra S. Brittingham
*Attorney, Agent, or Firm*—Vidas Arrett & Steinkraus

[57] ABSTRACT

A stent made of biodegradable material includes a drug that is released at a rate controlled by the rate of degradation of the biodegradable material. The stent includes a main body of a generally tubular shape. The main body may further include a plurality of apertures extending therethrough and a slot defined by opposing edges which permits insertion and positioning of the stent.

5 Claims, 2 Drawing Sheets

BIODEGRADABLE DRUG DELIVERY VASCULAR STENT

This is a continuation Ser. No. 08/013,145 filed on Feb. 1, 1993, now abandoned, which is a continuation of application Ser. No. 07/771,655 filed on Oct. 4, 1991, now abandoned.

BACKGROUND OF THE INVENTION

This invention relates to a device for providing mechanical support to a vessel lumen of a living being.

A variety of medical situations requires the use of a mechanism to expand and support a constricted vessel and to maintain an open passageway through the vessel. A few examples of such situations following angioplasty include holding a dissection in place, preventing closure during spasm, and preventing acute closure due to thrombosis. In these situations, devices, commonly known as stents, are useful to prevent stenosis of a dilated vessel, or to eliminate the danger of occlusion caused by "flaps" resulting from intimal tears that may be associated with angioplasty, or to hold two ends of a vessel in place.

Stents have been made using materials of varied composition and conformation. McGreevy et al U.S. Pat. Nos. 4,690,684 and 4,770,176 describe a meltable stent that is inserted into the interior of the ends of a blood vessel during anastomosis. Anastomosis refers to the surgical or physical connection of two tubular structures, such as veins or arteries. The stent is made of blood plasma, which is biologically compatible with the living being and which melts rapidly in response to heat.

The Fischell et al U.S. Pat. No. 4,768,507 describes an intravascular stent which is an unrestrained coil spring having an outside diameter of 2 to 12 millimeters and a length of 5 to 25 millimeters. The materials of construction are stainless steel, and a titanium alloy. Decreased thrombogenicity is achievable by coating the outside of the coil with a non-thrombogenic material such as ULTI carbon.

The Leeven et al U.S. Pat. No. 4,820,298 describes a stent having a flexible tubular body made from a thermal plastic to the form of a helix. Polyester and polycarbonate copolymers are selected as particularly desirable materials.

The Wolff et al U.S. Pat. No. 4,830,003 describes a stent made from wires formed into a cylinder. The wires are made of a biocompatible metal. Biocompatible metals include 300 series stainless steels such as 316 LSS, as well as platinum and platinum-iridium alloys, cobalt-chromium alloys such as MP35N, and unalloyed titanium.

The Wiktor U.S. Pat. No. 4,886,062 describes a stent made from low memory metal such as a copper alloy, titanium, or gold. The stent is preformed into a two-dimensional zig-zag form creating a flat expandable band.

The Gianturco U.S. Pat. No. 4,907,336 describes a wire stent having a cylindrical shape that results from an expandable serpentine configuration. Malleable materials of construction are preferably included from the group of annealed stainless steels, tungsten and platinum.

Goldberg et al, Canadian Application 2,025,626, describe a bio-degradable infusion stent used to treat ureteral obstructions. The application describes an extruded material of construction made of epsilon-caprolactone (15–25% w/w of terpolymer composition); glycoside (5–50% w/w) and L(−)lactide (45–85% w/w). This material was described as having a minimum tensile strength of at least 500 pounds per square inch, preferably 650 psi; elongation of greater than 10%, preferably greater than 100%; and Shore A hardness equal to 50–100%, preferably 75–95%. The Goldberg et al patent application describes a method for incorporating radiopaque materials such as barium sulfate into the polymer in amounts ranging from 5–30%. The mechanism of biodegradation is described as hydrolysis resulting in degradable products excreted in urine or reabsorbed into tissues. The duration of functional life of the stent is estimated at about 3–7 weeks.

The Wilcoff U.S. Pat. No. 4,990,155 describes a plastic stent having an inherently expandable coil conformation. The "inherency" results from an elastic memory conferred by electron beam radiation imparting cross-linkages that provide an inherent tendency to return to a given diameter after any distortion. Materials of construction include high density polyethylene. Optionally, this material is compounded with an anti-coagulant and/or an x-ray opaque material such as bismuth-sub-carbonate.

The Shockley et al U.S. Pat. No. 4,994,033, describes a drug delivery dilatation catheter having three flexible, plastic tubes concentrically arranged relative to each other. The outermost sleeve of this catheter contains microholes for drug delivery. These microholes are made with a laser beam. Drugs that can be delivered by this system include aspirin, persantin, heparin, and prostaglandins. Drugs are delivered when externally applied pressure causes the innermost sleeve to balloon out. The drug is then forced through the microholes to spray and to treat a lesion.

Sigwart, Canadian Patent Application 2,008,312, describes a stent made from a malleable flat sheet having a reticulated pattern. The reticulated pattern includes non-deformable squares or diamonds. The stent is made by rolling the sheet and locking the sheet into a spiral having a small diameter. The sheet is locked into a spiral by a tie interwoven into the reticulated pattern. Once inserted into the lumen of a vessel, the spiral is expanded and held in place by flaps integrated into the outer body of the stent.

The stents mentioned do not remedy all problems relating to stents. In particular, some uses require stents to safely degrade within the bloodstream of an artery or vein over a period of weeks to months. Such stents must meet particular criteria. For instance, such stents must be compatible with surrounding tissue in the vein or artery as well as with blood flowing through the vein or artery. Degradation products must be prevented from forming emboli.

Stents should also optimize flow through a vein or artery. Additionally, there is a need for stents which deliver agents or drugs to blood passing through the vein or artery that are generally beneficial to the recipient. Also desired are stents which can deliver drugs or biologically active agents at a controlled rate to blood passing through the vessel lumen as well as to the vessel wall.

SUMMARY OF THE INVENTION

The present invention includes a biodegradable stent for insertion into a lumen of a vessel in a living being. The biodegradable stent is made from at least one biodegradable material that is also biocompatible and includes a drug which is released into the lumen of the vessel at a rate controlled by the rate of degradation of the biodegradable material.

DETAILED DESCRIPTION OF THE PREFERRED EMBODIMENTS

Figure 1:
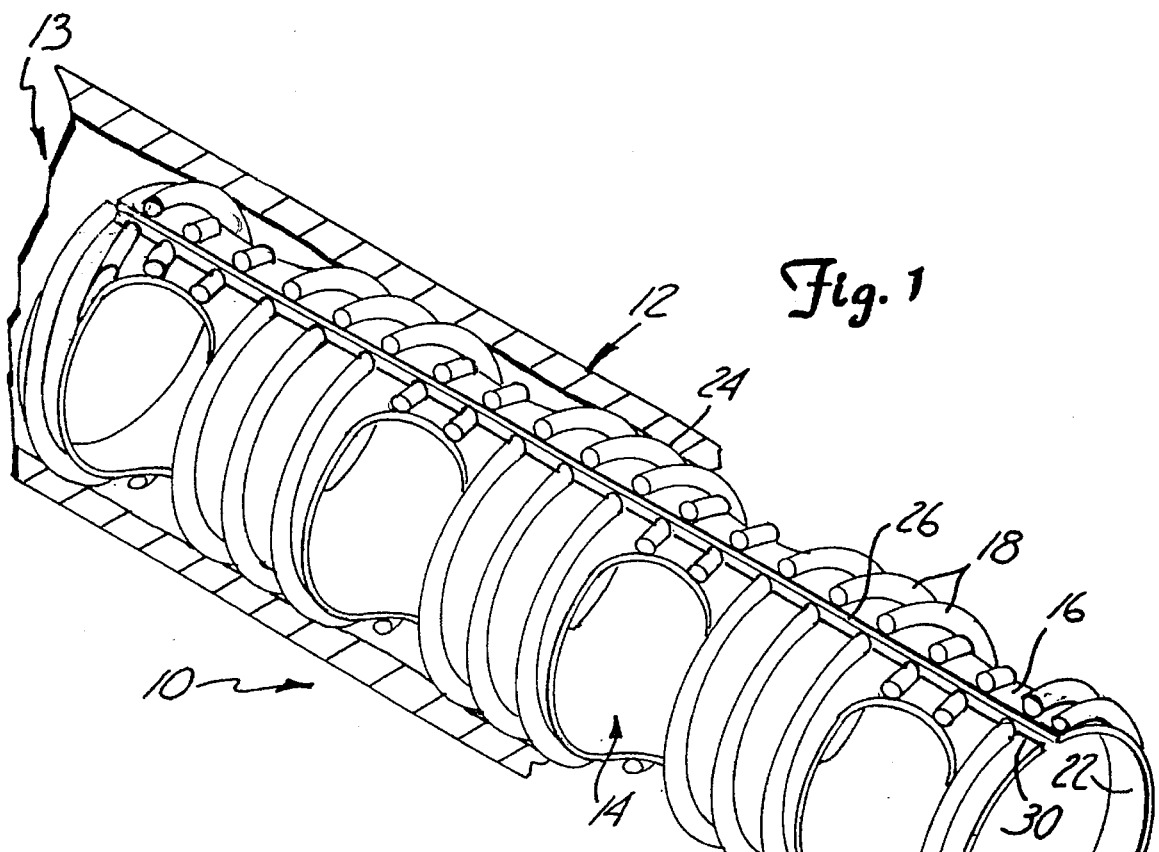
FIG. 1 is an enlarged perspective view of one embodiment of the stent of the present invention.

The present invention includes a biodegradable stent generally illustrated at 10 in FIG. 1. The stent 10 releases drugs into a tubular vessel 12 having a lumen 13 in a living being. The rate of drug release is controlled by the rate of degradation of the biodegradable materials. The stent 10 also provides mechanical support to a tubular vessel 12 in a living being. The stent strengthens an area of the vessel that is in contact with the stent 10.

The stent 10 includes a generally tubular main body 11 and a plurality of fibers 18 disposed around the main body 11. A plurality of apertures 14 extend through the stent 10. The stent 10 also includes a slot 26 extending the length of the stent.

Figure 2:
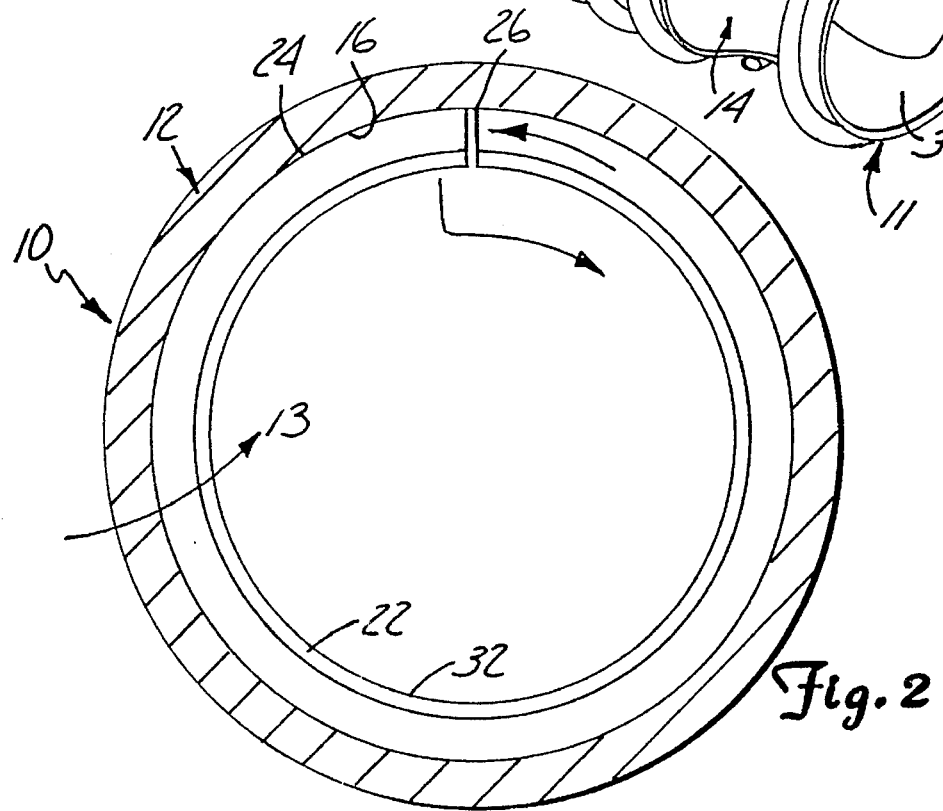
FIG. 2 is a cross-sectional view of the stent.

The tubular main body 11 includes an outer surface 16 and inner surface 22. The outer surface 16 of the main body 11 faces an inner surface wall 24 of the vessel 12. The inner surface 22 of the stent 10 faces a stream flowing through the lumen 13 as shown in cross section in FIG. 2. The stent of the present invention may range from 1 millimeter in diameter to 50 millimeters in diameter and from 1 millimeter in length to 50 millimeters in length. The size of the stent is dictated by the lumen of the vessel to which the stent is placed. The tubular main body suitably has a length of up to approximately 5 centimeters.

The plurality of fibers 18 disposed around the main body 11 contacts the outer surface 16 of the main body. In one preferred embodiment, the fibers are arranged concentrically around the main body, encircling the outer surface 16 in an annular alignment. The annular alignment is ordered so that individual fibers are separated by approximately the same distance. Alternatively, the fibers are arranged in annular pairs or triplets. In another alternative embodiment, the plurality of fibers abut each other in annular alignment.

In another alternative embodiment, the plurality of fibers 18 of the outer surface are braided. Braided fibers are also arranged in annular alignment around the main body of the stent 10. In one other alternative embodiment, the fibers are woven. Woven fibers increase the stretch and flexibility of the stent compared to fibers which are not woven. Solid fibers, hollow fibers, or a combination thereof can be used for any of the embodiments described above.

The plurality of fibers 18 of the main body 11 can be formed by techniques well known in the art. These techniques include melt, wet and dry spinning. High molecular weight polymers having a range of 200,000 to 3,000,000 daltons are preferred for successful fiber production. One example of a biodegradable material meeting this criterion for fiber manufacture is poly-L-lactide.

The fibers generally undergo further orientation in the extruded direction. One technique for orienting the fibers is to stretch the fibers at a temperature range of 50° to 150° C.

Desirably, the plurality of fibers 18 disposed around the main body 11 of the stent 10 have an outer diameter not exceeding approximately 0.2 millimeters. In the case of hollow fibers, the wall thicknesses should be within the approximate range of 25 to 100 microns. Preferably, the fibers should have a tensile strength in a range of 4,000 to 500,000 pounds per square inch and have a modulus of 200,000 to 2,000,000 pounds per square inch.

In one embodiment, the main body includes a film that is preferably combined with the plurality of fibers disposed around the main body 11. The film combined with the plurality of fibers defines the outer surface 16 of the main body. The plurality of fibers can be combined with the film using any number of conventional methods. In one conventional method, solvation sealing, the steps of heat pressing and extrusion molding combine the film and fiber production into one step for the orientation of the polymer materials. Additional methods include solvent sealing of the fibers to the film or heat melting processes for the annealing of the multiple layers. By the solvation sealing method, fibers and film are combined to form the outer surface into a single biodegradable material matrix.

Preferably, the main body 11 of the stent 10 includes a film 32, covering the inner surface 22. The film of the inner surface 22 is formed by conventional methods such as heat or pressure extrusion or solution casting.

Additionally, the present invention includes an embodiment where the inner surface 22 and the outer surface 16 of the main body 11 are separated by at least one interior film layer. The interior film layer is integrated into the main body by multiple casting with the inner and outer surfaces. The present invention further includes a main body having more than one biodegradable interior film layer. Desirably, the thickness of the main body does not exceed approximately 0.25 millimeters.

The plurality of apertures of the present invention is preferably ordered around the main body to form rows of apertures. FIG. 1 illustrates two rows of apertures, the length of each row extending the length of the tubular main body. In an alternative embodiment, the plurality of apertures are ordered to form one row having a length extending the length of the tubular main body. The apertures within the one row are bounded by edges 28 and 30 bordering the slot 26. In one other alternative, the plurality of apertures are ordered to form a row extending less than the length of the main body of the stent. In another alternative embodiment, the plurality of apertures are not ordered but are located randomly over the main body of the stent.

Suitable shapes for the individual apertures include both asymmetrical and symmetrical shapes such as ovals, circles, or rectangles. Also, apertures may be made in a variety of sizes. The apertures can be formed by any conventional means such as stamping.

Figure 3:
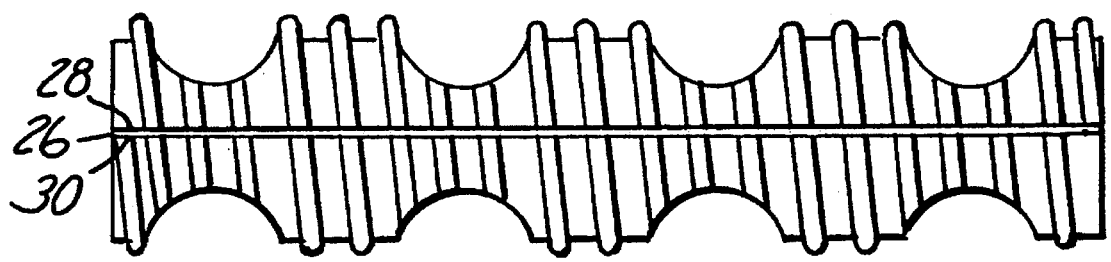
FIG. 3 is an overview of one embodiment of opposing edges bounding a slot extending lengthwise along the main body of the stent of the present invention.

The slot 26 extends the length of the stent and is defined by opposing edges 28 and 30 of the main body as illustrated in FIG. 3. In a preferred embodiment, the fibers 18 are oriented fibers and are fixed to the outer surface 16 of the main body 11. When the slot 26 is formed, the oriented fibers 18 provide a spring force in an outward substantially radial direction. The outward spring force increases the effective diameter of the main body while the slot permits compression or reduction of the effective diameter. Once formed, the stent is normally at its effective maximum diameter and the slot is at its widest.

In use, the stent is positioned at the inner surface wall 24 of the vessel 12 by radially compressing the stent to a tubular diameter less than the diameter of the vessel 12 and moving the stent to a desired site within the vessel. The stent is secured by releasing the stent from compression so that the stent can radially spring out to abut against the inner surface wall 22 of the vessel 12.

In the most preferred embodiment, the biodegradable stent of the present invention is made of biodegradable materials that are also biocompatible. By biodegradable is meant that a material will undergo breakdown or decomposition into harmless compounds as part of a normal biological process. It is important to the present invention that the plurality of apertures 14 in the main body 11 of the stent promote the successful biodegradation of the stent 10. Optimally, the plurality of apertures 14 permits epithelial cells to grow on the stent 10. It is believed that the epithelial cell growth will encapsulate particles of the stent during biodegradation that would otherwise come loose and form emboli in the blood stream.

Suitable biodegradable materials for the main body 11 of the stent 10 of the present invention include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Biodegradable glass or bioactive glass is also a suitable biodegradable material for use in the present invention. Preferably the materials have been approved by the U.S. Food and Drug Administration.

The present invention includes a biodegradable stent incorporating a variety of biodegradable materials within it. For instance, in one embodiment, the film and fibers covering the inner surface 22 of the main body 11 of the biodegradable stent is made of either polylactic acid, polyglycolic acid (PGA), collagen or other connective proteins or natural materials, polycaprolactone, copolymers of these materials as well as composites thereof and combinations of other biodegradable polymers. The film covering the outer surface 16 along with the plurality of fibers 18 are made of either collagen, hylauric acid, adhesive proteins, copolymers of these materials as well as composites and combinations thereof. The present invention includes an embodiment where fibers are made from more than one biodegradable material. Also, the present invention includes an embodiment where the film is made from a biodegradable material different from the fibers.

One advantage of using the variety of biodegradable materials within the main body of the stent is control of degradation. Biodegradable materials degrade at different rates, ranging from weeks to several years. Consequently, the presence of different biodegradable materials in the stent permits the stent to degrade in a predictable, orchestrated fashion.

The stent of the present invention further includes incorporation of a drug or drugs or other biologically active materials. The drugs are contained within the biodegradable materials of which the stent is composed. As the stent biodegrades, drugs are administered to the surrounding tissue or to the blood stream. Thus, the rate of drug release is controlled by the rate of degradation of the biodegradable materials. A material that degrades rapidly will release the drug faster than a material that degrades slowly.

Drugs are incorporated into the biodegradable stent using techniques known in the art. The techniques include simple mixing or solubilizing with polymer solutions, dispersing into the biodegradable polymer during the extrusion of melt spinning process, or coating onto an already formed film or fiber. In one embodiment, hollow fibers, which contain anti-thrombogenic drugs, are arranged in a parallel concentric configuration with solid fibers for added support for use on the outer surface 16 of the main body 11 of the stent 10.

Further, drugs can be incorporated into the film of both the inner and outer surfaces by using methods such as melting or solvation. If an interior film layer is present within the main body as well, the interior layer and inner and outer surfaces are then combined with each other such as by mechanically pressing one layer to the other layer in a process augmented by heat or solvation adhesives. Alternatively, drugs or biologically active agents are incorporated into the film layer and surfaces by entrapment between the layers and surfaces of biodegradable material sandwiched together, thereby further promoting release of the drugs or agents at different rates.

The drugs or other biologically active materials incorporated into the stent of the present invention perform a variety of functions. The functions include but are not limited to an anti-clotting or anti-platelet function; and preventing smooth muscle cell growth on the inner surface wall of the vessel. The drugs include but are not limited to drugs that inhibit or control the formation of thrombus or thrombolytics such as heparin or heparin fragments, aspirin, coumadin, tissue plasminogen activator (TPA), urokinase, hirudin, and streptokinase, antiproliferatives (methotrexate, cisplatin, Fluorouracil, Adriamycin, and the like) antioxidants (ascorbic acid, carotene, B, vitamin E, and the like), antimetabolites, thromboxane inhibitors, non-steroidal and steroidal antiinflammatory drugs, Beta and Calcium channel blockers, genetic materials including DNA and RNA fragments, and complete expression genes, carbohydrates, and proteins including but not limited to antibodies (monoclonal and polyclonal) lymphokines and growth factors, prostaglandins, and leukotrienes. The stent also incorporates bioactive materials such as fibronectin, laminin, elastin, collagen, and intergrins. Fibronectin promotes adherence of the stent to the tissue of the vessel 12.

In one specific example of a biodegradable material incorporating drugs, a poly-L-lactide having an intrinsic viscosity of 2.3 dl/g is used to form monofilament fibers using a spin or melt spinning process. Five percent aspirin or 5% heparin was incorporated into the melt of the poly-L-lactide prior to fiber formation. The fibers formed had a diameter of approximately 0.5 millimeters. The monofilaments were then stretched under temperatures ranging from 50° C. to 200° C. to orient the fiber. The temperature employed depends upon the kind of material used to make the fiber. The final diameter of the oriented fiber falls within a range of 0.1 to 0.3 millimeters. Similar processing was used to incorporate 5% aspirin or 5% heparin into poly-L-lactide and polyglycolide.

Just as the use of a variety of biodegradable materials facilitates a controlled degradation of the biodegradable stent, so similarly does the incorporation of a variety of drugs into the biodegradable materials facilitate control of drug release to perform a variety of functions. For instance, drugs released from the outer surface as the outer surface degrades facilitate adherence of the stent to the inner surface wall 24 of the vessel 12. Drugs released from fibers perform a variety of functions, ranging from promoting cell growth to altering the blood clotting mechanisms, depending upon from what fiber released. In one embodiment, drugs released from the inner surface 22 of the stent as the inner surface degrades temper platelet function in blood flowing through the lumen 13.

Although the present invention has been described with reference to preferred embodiments, workers skilled in the art will recognize that changes may be made in form and detail without departing from the spirit and scope of the invention.

What is claimed is:

1. A biodegradable self-expanding stent for insertion into a lumen of a vessel of a living being, the stent being substantially completely biodegradable the stent comprising:
(a) a generally tubular biodegradable main body surrounded by an array consisting of individual biodegradable materials having individual rates of degradation, the individual biodegradable materials contain a plurality of drugs, said drugs being released into the lumen of the vessel as the biodegradable materials degrade, at rates controlled by the rates of degradation of the biodegradable materials;
(b) said tubular main body including a slot extending lengthwise through the main body and defined by opposing edges of the main body wherein the opposing edges must be moved toward each other under compression in order to transport the biodegradable stent through a vessel of a living being; and said array being annularly aligned oriented fibers disposed about and attached to said tubular main body and so oriented to provide a self-expanding, spring force in an outward, substantially radial direction to increase the effective diameter of said main body.

2. The stent of claim 1 wherein the tubular biodegradable main body includes a plurality of layers made from art array consisting of individual biodegradable materials that degrade at different rates.

3. The biodegradable stent of claim 1 wherein the tubular biodegradable main body includes:

an outer surface having a generally tubular shape for contacting tissue of a vessel when the main body is placed in a living being; and a plurality of apertures extending through the main body.

4. A biodegradable, self-expanding stent for insertion into the lumen of a vessel of a living being, the stent being substantially completely biodegradable the stent comprising:
(a) a generally tubular biodegradable main body surrounded by an array consisting of individual biodegradable materials that degrade at different rates, said individual biodegradable materials containing a plurality of drugs, said drugs being released into the vessel lumen as the biodegradable materials degrade, said tubular body having an outer surface of generally tubular shape for contacting tissue of a vessel said array comprising annularly aligned oriented fibers disposed about and attached to said tubular main body and so oriented to provide a self-expanding, spring force in an outward, substantially radial direction to increase the effective diameter of said main body;
(b) a slot extending lengthwise through the main body and defined by opposing edges of the main body wherein the opposing edges must be moved toward each other under compression in order to transport the biodegradable stent through a vessel of a living being, said slot allowing compression of the main body to decrease its diameter; and
(c) a plurality of apertures extending through the main body.

5. The biodegradable stent of claim 4 wherein the fiber shape of the biodegradable materials is a hollow fiber shape and drugs are incorporated in the biodegradable materials enclosed within the hollow fiber shape.

* * * * *

UNITED STATES PATENT AND TRADEMARK OFFICE
CERTIFICATE OF CORRECTION

PATENT NO. : 5,464,450
DATED : November 7, 1995
INVENTOR(S) : Paul J. Buscemi, et al.

It is certified that error appears in the above-indentified patent and that said Letters Patent is hereby corrected as shown below:

Column 7, line 22, delete "art" and insert --an--.

Signed and Sealed this

Sixth Day of February, 1996

Attest:

BRUCE LEHMAN

Attesting Officer     Commissioner of Patents and Trademarks